US00PP21389P3

(12) United States Plant Patent

Maillard et al.

(10) Patent No.: US PP21,389 P3

(45) Date of Patent: Oct. 19, 2010

(54) FLAT PEACH TREE NAMED "FLATPRETTY"

(50) Latin Name: ***Prunus Persica* L. Batsch—White Flat peach**

Varietal Denomination: Flatpretty

(75) Inventors: Laurence Maillard, Elne (FR); Arsene Maillard, Elne (FR)

(73) Assignee: S.A.R.L. Agro Selection Fruits, Elne (FR)

( * ) Notice: Subject to any disclaimer, the term of this patent is extended or adjusted under 35 U.S.C. 154(b) by 1190 days.

(21) Appl. No.: 11/434,796

(22) Filed: May 17, 2006

(65) Prior Publication Data

US 2006/0265795 P1 Nov. 23, 2006

(30) Foreign Application Priority Data

May 18, 2005 (EP) ..... 2005-0906

(51) Int. Cl.

*A01H 5/00* (2006.01)

(52) U.S. Cl. ..... Plt./195

(58) Field of Classification Search ..... Plt./195

See application file for complete search history.

(56) References Cited

U.S. PATENT DOCUMENTS

PP16,836 P2 * 7/2006 Goffreda et al. ..... Plt./197

* cited by examiner

*Primary Examiner*—Susan B McCormick Ewoldt

(74) *Attorney, Agent, or Firm*—Westerman, Hattori, Daniels & Adrian, LLP

(57) ABSTRACT

A new and distinct variety of flat peach tree, denominated 'FLATPRETTY', has an early maturity and good fruit quality.

6 Drawing Sheets

Botanical classification: *Prunus persica* L. Batsch—White Flat peach.

Variety denomination: 'FLATPRETTY'.

BACKGROUND OF THE VARIETY

The present invention relates to a new and distinct variety of *Prunus persica* L. Batsch white flat peach tree. This new tree, named 'FLATPRETTY', produces semi-clingstone fruits of good eating quality for fresh market in July in the 66 — Pyrénées Orientales departement — France. Fruits also have a very long shelf life on the tree and after harvesting. Contrast is made to one of its parent, the 'MAILLARFLAT' (not patented) flat peach, for reliable description. The new variety was selected because of its characteristics, which are very similar to those of its parent 'MAILLARFLAT' (not patented) i.e. fruits of very good quality and even more attractive visually. However, the 'FLATPRETTY' variety has an early maturity. The fact that 'FLATPRETTY' ripens earlier than 'MAILLARFLAT' (not patented) might allow a continuous feeding of fruit markets in July-August with very similar fruits. Since 'MAILLARFLAT' (not patented) fruits were appreciated by consumers and resulted in a commercial success, 'FLATPRETTY' is considered as a commercially promising candidate.

ORIGIN OF THE VARIETY

'FLATPRETTY' flat peach tree originated in a cultivated area of the south of France, in the Pyrenees Orientales departement , where it was tested. This place is under a Mediterranean climate in a temperate area characterized by irregular and low precipitation with drought in summer, high temperatures all year long.

The 'FLATPRETTY' variety was obtained by controlled sowing after open-pollination of the 'MAILLARFLAT' (not patented) flat peach variety. Thus the seed parent was the 'MAILLARFLAT' (not patented) flat peach tree and the pollen parent is unknown. 'FLATPRETTY' was provisionally designated and tested as 01.10.64 PBPL and was registered at the Official Catalogue of the Agriculture Ministry of the French Republic on Dec. 29, 2004, under number 1016568. It was propagated by grafting on a Franc INRA Montclar® (not patented) rootstock tree. It has been determined to have unique tree and fruit characteristics making it worthy for commercial fresh fruit production. There are no known effects of the standard Franc INRA Montclar® (not patented) rootstock on the scion cultivar. Asexually propagated plants remained true to the original tree and all characteristics of the tree and the fruit were transmitted. The plant was reproduced asexually by us in Elne, Pyrénées-Orientales departement, France. The variety was also granted protection as a Community Plant Variety on Feb. 23, 2009, under N°EU24115.

SUMMARY OF THE VARIETY

The new and distinct variety of flat peach tree blooms in March at Perpignan in the Pyrenees Orientales departement, France. More particularly, it approximately blooms between the $5^{th}$ and $15^{th}$ of March, two days before the 'MAILLARFLAT' (not patented) flat peach variety. The new variety has a shorter blooming duration than the 'MAILLARFLAT' (not patented) variety: approximately 5 days shorter. Blooming dates vary slightly with the prevailing climatic conditions.

The first fruit of the 'FLATPRETTY' flat peach tree first ripens at the end of June or beginning of July, 25 days before the first fruit of the 'MAILLARFLAT' (not patented) flat peach tree. More particularly, it approximately ripens between June 28th and July 9th. Maturity dates vary slightly with the prevailing climatic conditions.

DESCRIPTION OF THE DRAWINGS

In the accompanying drawing, which are as nearly true as it is reasonably possible to make in a colour illustration of this type.

Figure 1:
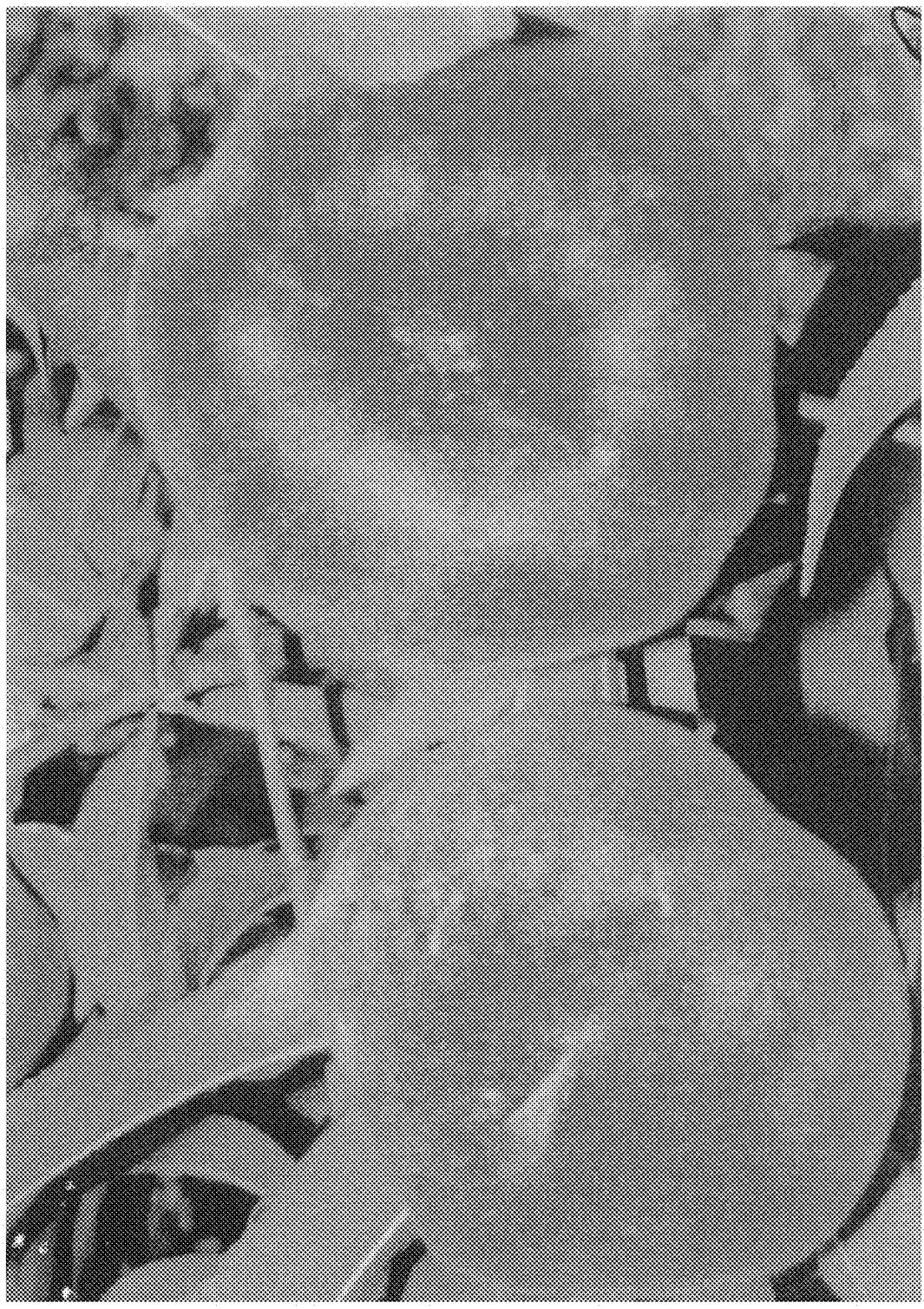
FIG. 1 is a colour photograph, which shows the flesh of the fruit of the new variety.
Figure 2:
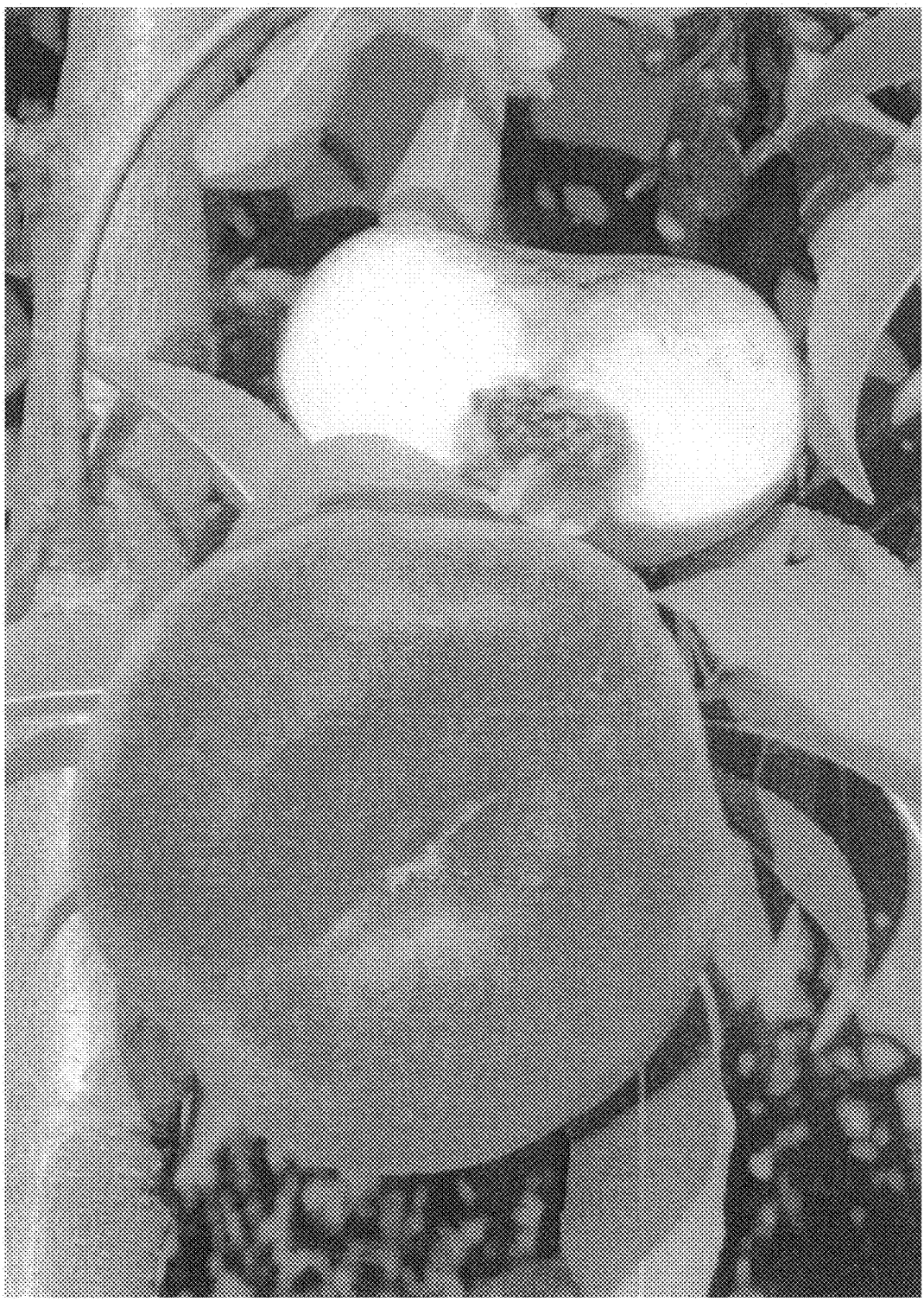
FIG. 2 is a colour photograph, which shows a typical specimen of the fruit of the new variety.
Figure 3:
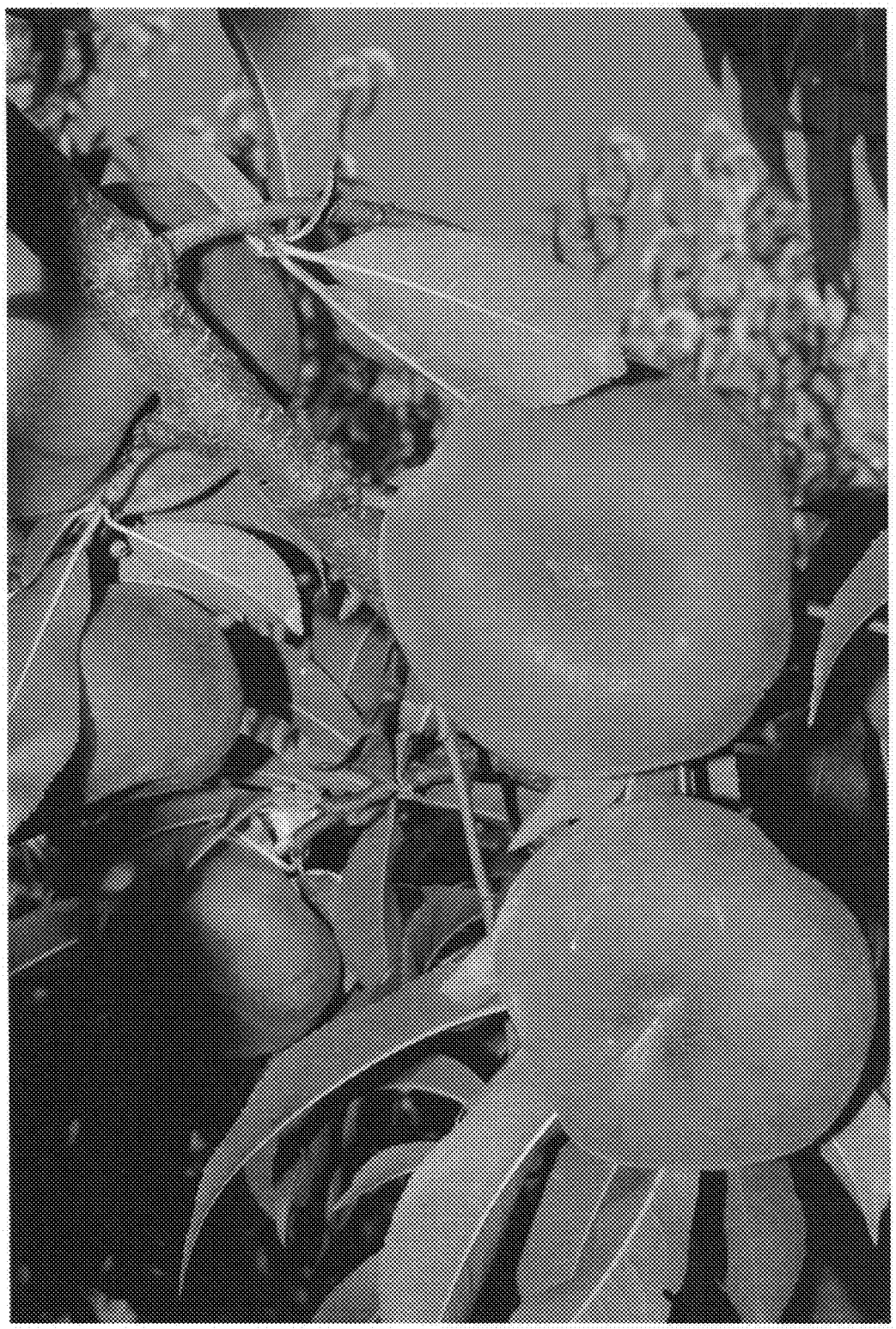
FIG. 3 is a color photograph, which shows a twig bearing typical fruit specimens of the new variety, and leaves of the new variety.
Figure 4:
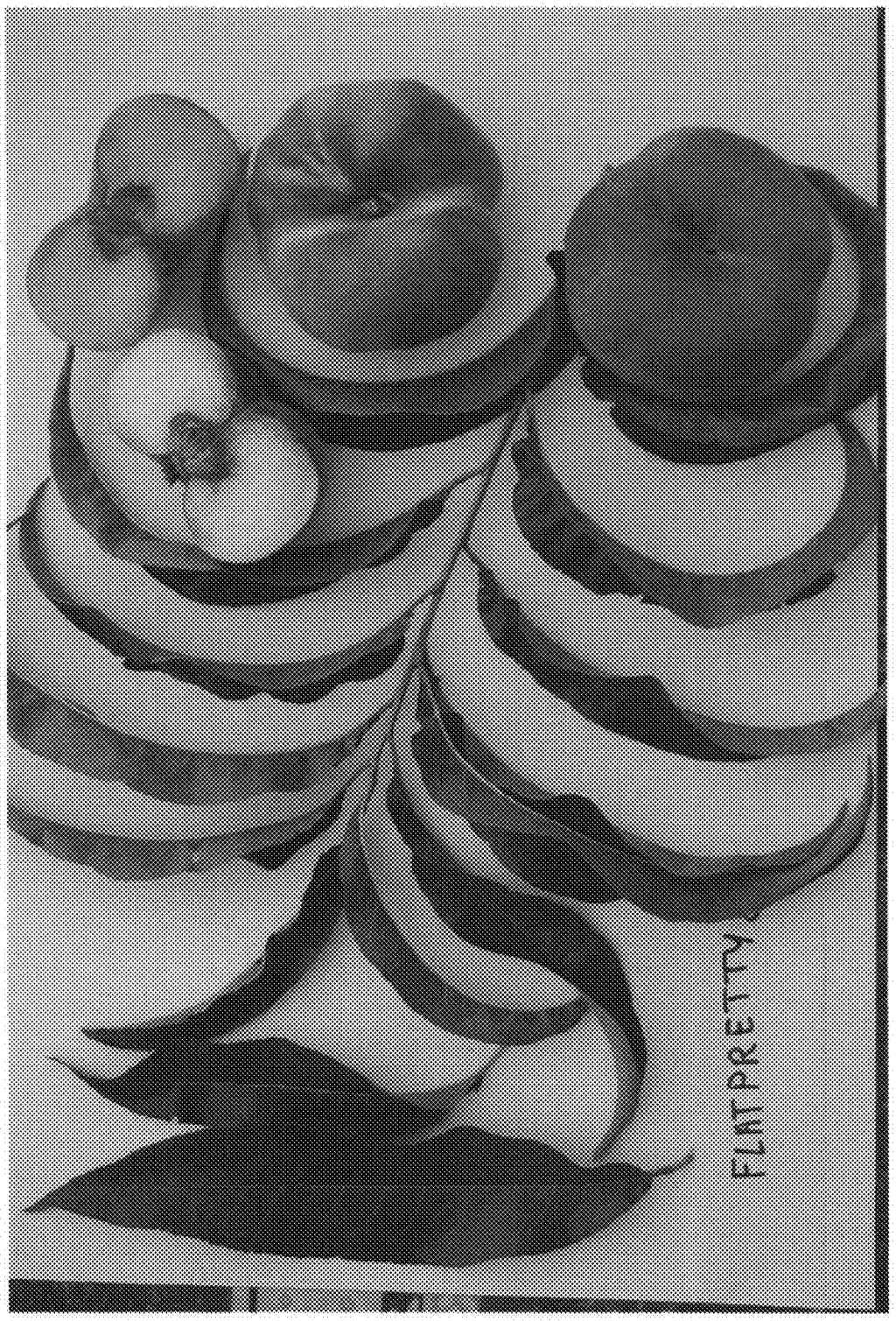
FIG. 4 is a color photograph, which shows two whole fruits of the new variety and a third fruit cut in half with the stone left in one of the halves for depicting the fruit flesh, the pit cavity and the stone of the new variety, as well as a twig depicting the leaves of the new variety.
Figure 5:
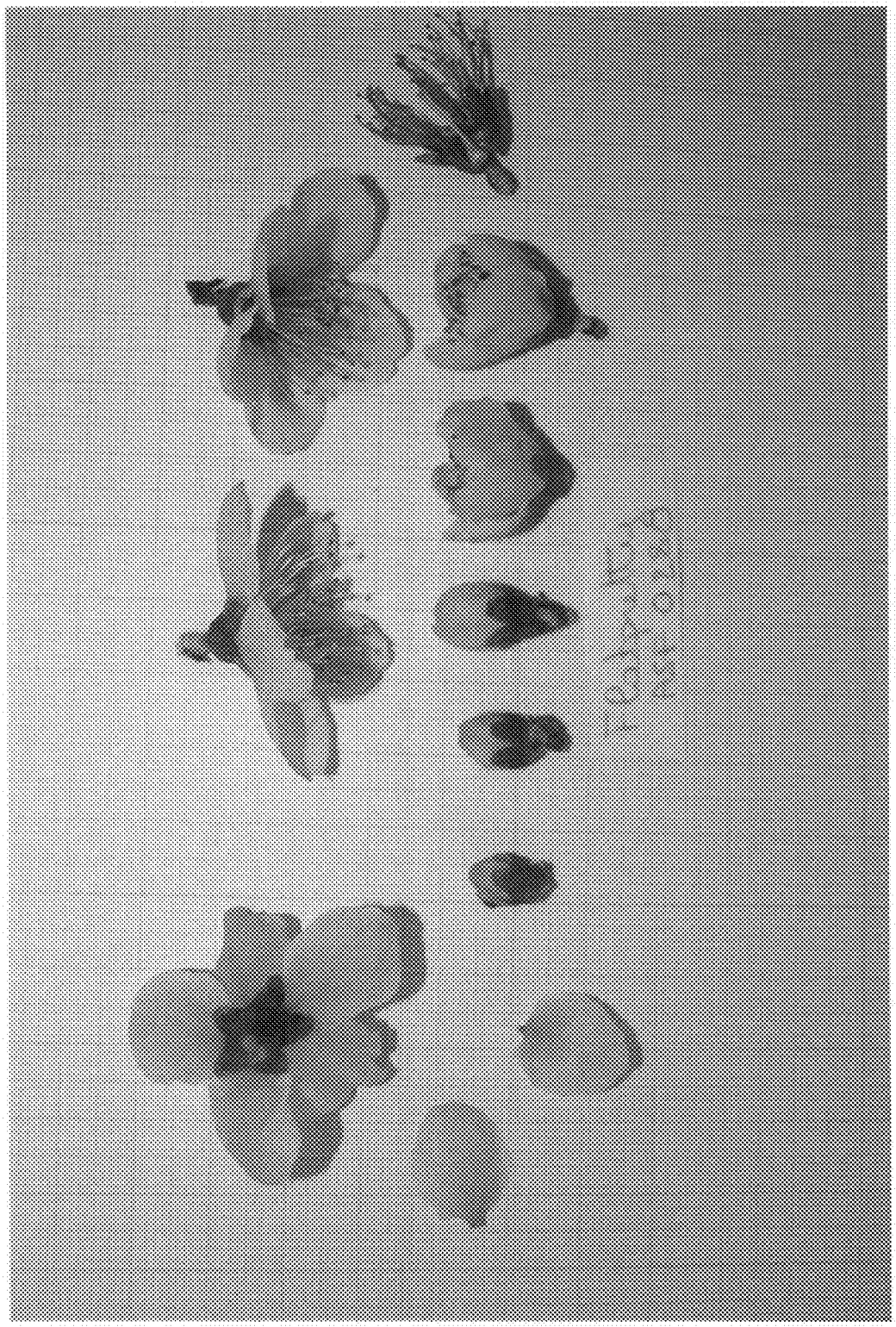
FIG. 5 is a color photograph with reverse and size views of flowers of the new variety, and, with petals removed, reproductive organs of the new variety.
Figure 6:
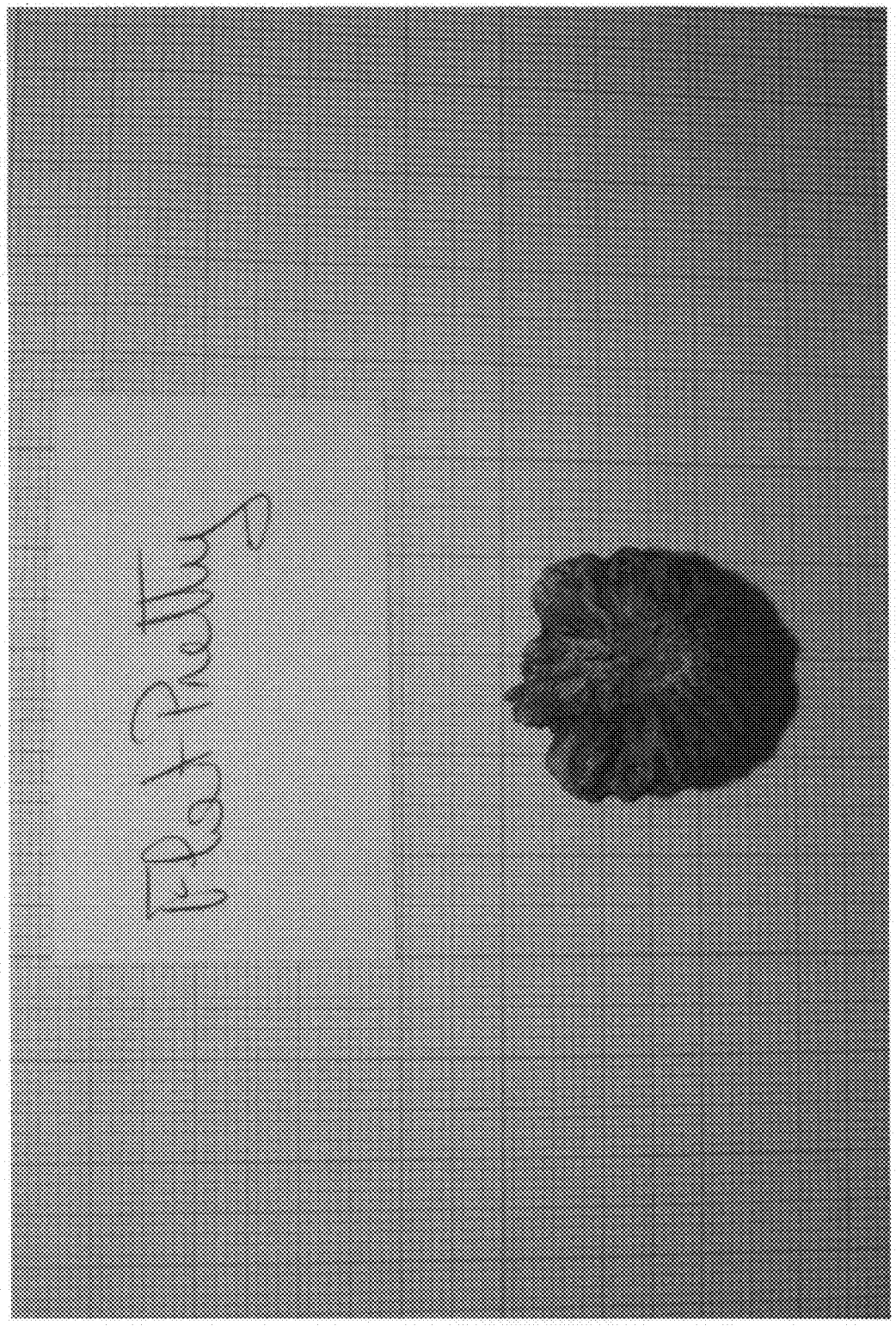
FIG. 6 is a color photograph, which shows a dried stone of the new variety.

Due to chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruit by 'FLATPRETTY' is high, due to its early ripening and evenness of maturity.

Trees are vigorous and of medium to large stature standing in a semi-spread to semi-upright aspect. The flowering shoot is present excluding brushwoods side away from the sun. Flowering begins medium in springtime. The type of flower is showy with relative medium petal size. Petals are medium pink. Two or three reniform leaf glands are present. Time of maturity for consumption is early. The fruit flesh is white and its skin has a bright red blush. The stone is small and the flesh is semi-adherent to the stone.

Compared to the 'MAILLARFLAT' (not patented) variety, 'FLATPRETTY' has an earlier maturity, 25 days before. FLATPRETTY fruits red blush covers 80 to 90% of fruit skins instead of 60 to 70% for the 'MAILLARFLAT' (not patented) variety. Fruits are less embossed than 'MAILLARFLAT' (not patented) fruits and generally more appealing. Productivity, blooms and taste are the same as those of the 'MAILLARFLAT' (not patented) variety.

DETAILED DESCRIPTION

Referring more specifically to the pomological details of this new and distinct variety of flat peach tree, the following was observed, if not differently specified, during the 2008 growing season under the ecological conditions prevailing at the orchards located near the town of Elne, Pyrenees-Orientales departement, France. All observations were done on rootstock cultivars. The rootstock was a 'Franc Inra Montclar®' (not patented) tree. All major color code designations are by reference to The R.H.S. Color Chart (Fourth Edition) provided by The Royal Horticultural Society of Great Britain.

TREE

Size:

*Generally.*—Considered medium to large as compared to other common commercial flat peach cultivars ripening early. The tree size the first year was approximately 280 cm. The tree was pruned during each following dormant season to a height of approximately 250 cm. Current season shoots growth could reach 80 cm. So the tree size from the second year (second and next years) reached a final height of 330 cm with current season shoots length comprised.

Spread: Approximately 100 cm with a cylindrical shape. The whole orchard was oriented to a central leader organisation, with tree lines spaced of 4.0 meters and trees spaced of 1.0 meter in a same tree line. As a result, the orchard contains 2500 trees by hectare.

Vigor: Considered vigorous.

Productivity: Very Productive. Fruit set is spaced by thinning to develop the remaining fruit into the desired market sized fruit. The number of the fruit set varies with the prevailing climatic conditions, and cultural practices employed during the bloom period, and is therefore not distinctive of the present variety.

Bearer: Very regular. Fruit set has been heavy during the years of observation and thinning of 1 fruit on 3 to 2 fruits on 3 was necessary every year during the past 5 years.

Form: The 'FLATPRETTY' variety has naturally a semi-spread to semi-upright shape.

Density: Considered dense.

Hardiness: The present tree was grown and evaluated in France. The variety appears to be hardy under typical central Pyrénées Orientales departement climatic conditions. Experimentations on different sites with winter chilling requirement comprised between 350 and 1200 hours showed a good behavior of the tree in all cases. Ascertained temperatures as low as −12 degrees Celsius in winter caused no damages to the tree. The tree was also very resistant to frosty springtime weather.

TRUNK

Diameter: Approximately between 6.5 and 7.7 cm in diameter when measured at a distance of approximately 30 cm above the soil level.

Bark texture: Considered slightly rough.

Lenticels: Numerous lenticels are present. The lenticels range in size from approximately 3 to 5 mm in width, and are about 1.5 mm in height.

Lenticel colour: The outside of lenticels has a silver-grey color (varying from RHS Grey 201D to RHS Black 202D), whereas the inside is considered brown (RHS Greyed Orange 166B).

Bark colouration: The bark has a silver-grey color a little darker than the lenticels (varying from RHS Grey 201C to RHS Black 202C).

BRANCHES

Size: Mature branches are considered medium to thick for the variety. Current season shoots are considered medium for the variety.

Diameter: Average as compared to other flat peach varieties. The current season shoots have a diameter from 4.0 to 8.0 millimeters, and branches of trees have a diameter comprised between 16.0 and 24.0 millimeters.

Surface texture: Average, wood which is several years old has no furrowed appearance.

Crotch angles: Primary branches are considered variable, but the crotch angles are generally between 60 and 73 degrees from the horizontal axis. This particular characteristic is not considered distinctive of the variety, however.

Current season shoots:

*Surface texture.*—Substantially glabrous.

Internode length: Generally 22.0 to 30.0 millimeters.

*Colour.*—The color of new shoots is considered a light green (varying from RHS Green 144A to C) on lower part of new shoots, whereas the upper part is colored in reddish brown (varying from RHS Greyed Red 187A to B to RHS Greyed Red 182A to C), depending on the location on the shoot and sunlight exposition.

Mature branches:

*Colour.*—Considered a Medium grey-brown (varying from RHS Grey Brown 199A to B).

LEAVES

Size: Considered medium to large for the species. Leaf measurements have been taken from mature leaves. The ratio leaf length/leaf width is generally between 3.6 and 3.8.

Leaf length: Approximately 140 to 168 millimeters without the petiole.

Leaf width: Approximately 38 to 46 millimeters.

Leaf base shape: Concave.

Leaf form: Lanceolate.

Leaf tip form: Acuminate and small.

Leaf colour:

*Upper leaf surface.*—Dark Green (RHS Green 137A).

*Lower surface.*—Medium Green (varying from RHS Green 137B to 137C).

Leaf texture: Smooth and glabrous.

Leaf venation: Pinnately veined.

Mid-vein:

*Colour.*—Light yellow green (RHS Yellow Green 145D).

Leaf margins: Slightly undulating.

Form: Considered slightly dentate.

Uniformity: Leaves are isolated or grouped by 2 or 3 with different sizes: one leaf of normal size with one or two smaller leaves (size-reduction of 50% and more).

Leaf glands:

*Size.*—Considered medium, about 1.5 millimeters.

*Number.*—Generally between 2 and 3.

*Type.*—Reniform.

*Colour.*—On young leaves, leaf glands color is considered a pale green (RHS Green 145B). On older leaves, leaf glands color turns to a dark brown (varying from RHS Grey Brown 199A to 199B).

Leaf stipules:

*Generally.*—No leaf stipules were observed. But as seen in the characteristic relative to the leaves uniformity, it is possible to find leaves by groups of 2 or 3, with a normal-size leaf and smaller ones.

FLOWERS

Flower buds:

*Generally.*—At pre-floral stage of development, the floral buds are conic in form with a round tip. Their form is evolving until blooming, with variables dimensions. Just before blooming, floral buds are approximately 12.0 millimeters wide and approximately 18.0 millimeters long.

*Colour.*—This characteristic is dependent upon the proximity to bloom. At pre-floral stage of development, the bottom of the flowers buds, formed by sepals, is of purple-brown color (RHS Greyed Purple 183A to C); the corolla, formed by petals, is generally of pink color (varying from RHS Red Purple 65A to B). Petals color shows an evolution until the end of flowering.

Hardiness: The buds are considered hardy under typical central Pyrénées Orientales departement climatic conditions. No winter injury was noted during the last several years of evaluation in the central Pyrénées Orientales departement, with winter temperatures as low as −12 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

Date of bloom: Generally March. The first bloom, observed on Feb. 24, 2002, was exceptionally early. Second and third bloom took place respectively on Mar. 10, 2003 and Mar. 5, 2004.

Blooming time: Considered middle-season in relative comparison to other commercial peach cultivars grown in the Pyrénées-Orientales departement, France. The date of full bloom is observed on March, more particularly — and generally — between March $5^{th}$ and March $15^{th}$. Observed blooming time were from Feb. 24, 2002 to Mar. 5, 2002, then from Mar. 10, 2003 to Mar. 22, 2003, and from Mar. 5, 2004 to Mar. 15, 2004. The date of bloom varies slightly with climatic conditions and cultural practices.

Duration of bloom: Approximately 12 days. This characteristic varies slightly with the prevailing climatic conditions.

Flower type: The variety is considered to have a showy type flower.

Flower size: Flower diameter at full bloom is generally from 36.0 to 41.0 millimeters.

Bloom quantity: Considered abundant, approximately about 40 flowers per meter.

Flower bud frequency: Generally 2 flower buds appear per node, occasionally one.

Petal size:

*Generally.*—Considered medium for the species.

Length: Generally about 18.5 millimeters.

Width: Generally about 17.0 millimeters.

Petal form: Rounded.

Petal count: Generally 5.

Petal texture: Smooth and glabrous.

Petal colour: Medium Pink (RHS Red Purple 65A to B) when young, slightly darkening with advancing senescence.

Fragrance: Slight.

Petal claw:

*Form.*—The claw is considered to have a conic form with a slighty rounded tip.

*Length.*—Approximately 5.0 to 6.0 millimeters.

*Width.*—Approximately 4.0 to 5.0 millimeters.

Petal margins: Generally very slightly undulated.

Petal apex:

*Generally.*—The petal apices are generally dome-shaped, thus with a rounded tip.

Flower pedicel:

*Length.*—Considered medium-long and having an average length of approximately 4.0 millimeters.

*Diameter.*—Considered average, approximately 2.0 millimeters.

*Colour.*—Brown to Light Brown (varying from RHS Grey Brown N199C to D).

Floral nectaries:

*Colour.*—A greenish yellow (ranging from RHS Yellow Group 13A to B to RHS Yellow Green 150A to B).

Calyx:

*Internal surface texture.*—Smooth and glabrous.

*Color.*—The outer surface of the calyx is considered of Purple-brown (RHS Greyed Purple 183B to D) color.

Sepals:

*Surface texture.*—The outer surface has a short, fine pubescent texture.

*Size.*—Average in size, and ovate in form.

*Colour.*—A Purple-brown (RHS Greyed Purple 183B to D).

Average number of stamens per flower: Approximately 40 to 45 stamens per flower.

Anthers:

*Generally.*—Average in length.

*Color.*—Orange-Yellow (varying from RHS Yellow Orange 16A to B). Anthers are becoming brown after maturity (RHS Greyed Purple Group 178A).

Pollen production: Pollen is abundant and of good quality. It has a yellow color (varying from RHS Yellow Orange 17B to C). The present variety is considered self fruitful (self-pollinating).

Filaments:

*Size.*—Variable in length, approximately 11.0 to 17.0 millimeters in length. In all cases filament's length is superior to pistil's length.

Color: Considered light pink (varying from RHS Red Purple 62C to D) to darker pink (varying from RHS Red Purple 73A to B) with advancing senescence.

Pistil:

*Number.*—Generally 1.

*Generally.*—Average in size.

*Length.*—Approximately 13.0 to 16.0 millimeters including the ovary; Length generally smaller than filament's length.

*Colour.*—Considered a very pale green (varying from RHS Yellow Green 150D Group to RHS Yellow Green 151D Group).

*Surface texture.*—The variety has a glabrous pistil.

FRUIT

Maturity when described: Very firm ripe condition (shipping ripe).

Date of first picking: Jun. 30, 2002. The date of harvest varies slightly with the prevailing climatic conditions. The variety has an early date of maturity.

Date of last picking: Jul. 11, 2002. Generally occurs between the last week of June and the first week of July. The variety allows picking within a short period of generally 12 days. In 2002, picking was easily achieved through only 2 harvests within this short time period.

Size:

*Generally.*—Considered medium for the variety.

Average cheek diameter: Approximately 69.0 to 78.0 millimeters.

Average axial diameter: Approximately 36.0 to 47.0 millimeters.

Typical weight: Usually around 180.0 grams. This characteristic is high dependent upon the prevailing cultural practices, and therefore is not particularly distinctive of the variety.

Fruit form:

*Generally.*—Flat and rounded. The fruit is generally uniform in symmetry, viewed from pistil end, and very little embossed.

Fruit suture: Shallow, extending from the base to the apex. No apparent callousing or stitching exists along the suture line.

Suture:

*Colour.*—This has generally a color similar to the blush fruit color, a Pink Red (varying from RHS Red Group 47A to C).

Ventral surface:

*Form.*—Smooth.

Apex: Depressed.

Base: Shallow.

Stem cavity: Average depth of the stem cavity is about 0.5 to 0.6 cm. Average width is about 1.2 to 1.5 cm.

Fruit skin:

*Thickness.*—Considered thick and strong, and very tenacious to the flesh to tenacious to the flesh depending on stage of maturity.

*Texture.*—Slightly pubescent.

*Taste.*—Semi-sweet.

*Tendency to crack.*—Generally not observed.

Colour:

*Blush colour.*—This blush colour is generally a bright Red (varying from RHS Red Group 47A to B). The red blush covers between 80% and 90% of the fruit skin surface. The percentage of the blush on the fruit skin surface can vary, and is generally dependant upon the prevailing conditions under which the fruit was grown.

*Ground colour.*—Yellow Orange (RHS Yellow Orange Group 18D).

Fruit stem: Medium in length, about 4.0 millimeters.

Diameter: Approximately 3.5 millimeters.

Colour: Pale green (varying from RHS Yellow Green 145A to 145B).

Flesh:

*Ripens.*—Slowly and homogeneously. Moreover, the fruit has a long shelf-life on the tree.

*Texture.*—Very firm, very dense, juicy at harvest maturity stage.

*Fibers.*—Generally none observed.

*Aroma.*—Pronouced.

*Eating quality.*—Considered very good, aromatic.

*Flavor.*—Considered semi-sweet. The Brix is superior to 13.0 degrees. Acidity is comprised between 6 and 9 meq/100 ml. The flavor is considered aromatic. The flesh is juicy.

*Juice.*—Jucy to very juicy at complete maturity.

*Brix.*—Generally superior to 13.0 degrees in our orchards. This characteristic varies slightly with the number of fruit per tree; prevailing cultural practices; and the surrounding climatic conditions, and can be much more higher. Especially, the Brix can reach higher values in warm and sunny areas i.e. in Spain.

*Flesh colour.*—White (RHS White Group N155D) with a slight red pigmentation (RHS Red Purple 60A to B) close to the stone.

STONE

Type: Semi-clingstone.

Size: Considered small for the variety.

Length: Approximately between 20.0 and 25.0 millimeters.

Width: Approximately between 20.0 and 24.0 millimeters.

Diameter: Approximately between 12.0 and 15.0 millimeters.

Form: Flat.

Base: Straight.

Apex:

*Shape.*—The stone apex has a flat tip.

Stone cavity: Considered small size, with dimensions corresponding to stone's dimensions.

Stone surface:

*Surface texture.*—The pit is transversely furrowed on its entire surface. Furrows are more pronounced and more flat toward lateral faces.

*Ridges.*—The surface texture is generally characterized by more prominent ridges along the ventral edges and is more prominent at the apical tip.

Ventral edge:

*Width.*—Considered small.

Dorsal edge:

*Shape.*—Grooved.

Stone colour: The color of the dry stone is generally considered an Orange to Red Brown (varying from RHS Greyed Orange 173B to D).

Tendency to split: Splitting is absent or very low, depending on climatic conditions between blooming period and stone hardening.

Kernel:

*Size.*—The kernel is considered small.

*Length.*—About 7.0 millimeters.

*Thickness.*—About 5.0 millimeters.

*Form.*—Considered flat and and elliptic.

*Pellicle.*—Pubescent.

*Colour.*—The kernel skin is a light yellowish orange (RHS Greyed Orange 166C). The almond is cream-white (RHS Orange Chite 159D). The kernel and its embryo are mature at the time of fruit maturity.

Use: The subject variety 'FLATPRETTY' produces very tasty semi-sweet fruits that are considered very firm, and attractively coloured. Fruits are excellent for uncooked consumption, crunchy or at full maturity, and very aromatic. They are useful for both local and very long distance shipping, with a shelf life of few weeks after harvest.

Keeping quality: Good. Fruits stayed a little more than one week on trees before harvest and then, has stored well until 2 to 3 weeks after harvest at 2.0 degree Celsius. They have a slow maturation and a long shelf life both on the tree after growth completion and after harvesting without alteration.

Shipping quality: Considered good. The fruit of the new flat peach variety showed minimal bruising of the flesh or skin damage after being subjected to normal harvesting and packing procedures.

Resistance to insects and disease: No particular susceptibilities were noted. The present variety has not been shown to be very sensitive to powdery mildew, or conservation diseases and decay due to its thick and strong skin.

Although the new variety of flat peach tree possesses the described characteristics when grown under the ecological conditions prevailing near the town of ELNE, FRANCE, it should be understood that variations of the usual magnitude and characteristics incident to changes in growing conditions, fertilization, pruning, pest control and horticultural management are to be expected.

We claim:

1. A new and distinct variety of flat peach tree as illustrated and described.

* * * * *